US007407709B2

(12) United States Patent
Zhou et al.

(10) Patent No.: US 7,407,709 B2
(45) Date of Patent: Aug. 5, 2008

(54) SILICONE PRESSURE SENSITIVE ADHESIVE AND ARTICLES

(75) Inventors: Zhiming Zhou, Woodbury, MN (US); Audrey A. Sherman, St. Paul, MN (US); Wayne K. Dunshee, Maplewood, MN (US); Wendi J. Winkler, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 250 days.

(21) Appl. No.: 10/744,212

(22) Filed: Dec. 22, 2003

(65) Prior Publication Data

US 2005/0136266 A1 Jun. 23, 2005

(51) Int. Cl.
*B32B 25/20* (2006.01)

(52) U.S. Cl. .................. 428/447; 525/474; 524/588; 528/28

(58) Field of Classification Search ............ 428/447; 525/474; 524/588; 528/28
See application file for complete search history.

(56) References Cited

U.S. PATENT DOCUMENTS

| 2,676,182 | A | 4/1954 | Daudt et al. |
| 3,627,851 | A | 12/1971 | Brady |
| 3,772,247 | A | 11/1973 | Flannigan |
| 3,890,269 | A | 6/1975 | Martin |
| 4,024,312 | A | 5/1977 | Korpman |
| 4,528,343 | A | 7/1985 | Kira |
| 4,661,577 | A | 4/1987 | Jo Lane et al. |
| 4,900,474 | A | 2/1990 | Terae et al. |
| 5,026,890 | A | 6/1991 | Webb et al. |
| 5,028,679 | A | 7/1991 | Terae et al. |
| 5,118,775 | A | 6/1992 | Inomata et al. |
| 5,214,119 | A | 5/1993 | Leir et al. |
| 5,236,997 | A | 8/1993 | Fujiki |
| 5,248,739 | A | 9/1993 | Schmidt et al. |
| 5,276,122 | A | 1/1994 | Aoki et al. |
| 5,314,748 | A | 5/1994 | Mazurek et al. |
| 5,461,134 | A | 10/1995 | Leir et al. |
| 5,512,650 | A | 4/1996 | Leir et al. |
| 5,516,581 | A | 5/1996 | Kreckel et al. |
| 5,580,915 | A | 12/1996 | Lin |
| 5,602,214 | A | 2/1997 | Lin et al. |
| 5,607,721 | A | 3/1997 | Ulman et al. |
| 5,670,598 | A | 9/1997 | Leir et al. |
| 6,355,759 | B1 | 3/2002 | Sherman et al. |
| 6,407,195 | B2 | 6/2002 | Sherman et al. |
| 6,441,118 | B2 | 8/2002 | Sherman et al. |
| 6,664,359 | B1 | 12/2003 | Kangas et al. |
| 2003/0152768 | A1* | 8/2003 | Melancon et al. ....... 428/355 R |

FOREIGN PATENT DOCUMENTS

| EP | 0 667 382 | 8/1995 |
| WO | WO 96/34029 | 10/1996 |
| WO | WO 96/35458 | 11/1996 |
| WO | WO 97/40103 | 10/1997 |
| WO | WO 98/17726 | 4/1998 |
| WO | WO 99/28540 | 6/1999 |
| WO | WO 03/052019 | 6/2003 |

OTHER PUBLICATIONS

Freeman, Silicones, Published for The Plastics Institute, (1962), p. 27.*
Encyclopedia of Polymer Science and Engineering, vol. 15, John Wiley & Sons, New York (1989), pp. 265-270.
Tyagi et al., "Segmented Organosiloxane Copolymers: 2. Thermal and Mechanical Properties of Siloxane urea Copolymers", *Polymer*, vol. 25, Dec. 1984.

* cited by examiner

*Primary Examiner*—Kuo-Liang Peng
(74) *Attorney, Agent, or Firm*—Carolyn A. Fischer

(57) ABSTRACT

Pressure sensitive adhesive compositions comprising an unreactive mixture of polydiorganosiloxane polyurea copolymer, diluent, and silicate tackifying resin. The compositions are useful for articles such as medical devices.

17 Claims, No Drawings

SILICONE PRESSURE SENSITIVE ADHESIVE AND ARTICLES

FIELD OF THE INVENTION

Pressure sensitive adhesive compositions comprising an unreactive mixture of polydiorganosiloxane polyurea copolymer, diluent, and silicate tackifying resin. The compositions are useful for articles such as medical devices.

BACKGROUND OF THE INVENTION

Various compositions based on polydiorganosiloxane polyurea copolymer have been described.

U.S. Pat. No. 5,580,915 describes silicone adhesive compositions having excellent quick stick, peel and tack adhesion properties. Generally the adhesive composition is the reaction mixture of a silanol-containing siloxane resin, a silicone polymer gum, and a silicone fluid containing functionality capable of reacting with silanol and silanol-like groups; optionally, a solvent and a cure catalyst are added.

EP 0 667 382 A1 describes a silicone pressure sensitive adhesive containing thermoplastic multi-segmented copolymer.

WO 97/40103 describes a composition that includes a silicone fluid, a silicone-urea segmented copolymers, and no more than about 30% by weight of a silicate tackifying resin.

WO 03/052019 describes pressure sensitive adhesives and methods, wherein the adhesives include a silicone tackifying resin and a polydiorganosiloxane polyurea copolymer. The tack of these adhesives is improved by the use of a processing as, such as a plasticizer.

Although, various compositions have been described, industry would find advantage in compositions particularly well-suited for medical applications wherein during use the adhesive is adhered to skin.

SUMMARY OF THE INVENTION

In one embodiment, the invention discloses an article, such as a medical device, comprising a substrate and a pressure sensitive adhesive composition disposed on the substrate. The adhesive composition comprises an unreactive mixture of polydiorganosiloxane polyurea copolymer, greater than 10 wt-% of a diluent, and greater than 30 wt-% silicate tackifying resin.

In another embodiment, the invention discloses an article comprising a substrate, a tie layer composition disposed on the substrate and a pressure sensitive adhesive composition disposed on the tie layer. The tie layer composition and the adhesive composition comprise a common base polymer and a common tackifying resin. The tie layer composition further comprises a reinforcement material. In some aspects, the tie layer comprises polydiorganosiloxane polyurea copolymer, a silicate tackifying resin, and polymeric fibers.

In each of the embodiments of the invention, the diluent and resin of the adhesive ale preferably free of functional groups that react with the components of the adhesive. Preferably, the polydiorganosiloxane polyurea copolymer is also substantially free of reactive end groups. The diluent is preferably a silicone fluid. The diluent is typically present in amount ranging from about 20 wt-% to about 50 wt-%. The diluent preferably has a weight average molecular weight of less than 50,000 g/mole. The amount of silicate tackifying resin is typically less than about 60 wt-%. The adhesive preferably has a storage modulus of no greater than about $1\times10^5$ Pa at about 25° C. Further, the initial peel force of the adhesive from polypropylene ranges from about 3 g/linear inch (2.54 cm) to 200 g/linear inch (2.54 cm).

DETAILED DESCRIPTION OF THE INVENTION

The present invention relates to an adhesive composition and articles, such as a medical device, comprising a substrate and the pressure sensitive adhesive disposed on the substrate. The adhesive composition comprises an unreactive mixture of at least one polydiorganosiloxane polyurea copolymer, greater than 10 wt-% of at least one diluent, and greater than 30 wt-% of at least one silicate tackifying resin.

Pressure-sensitive adhesive (PSA) compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as PSAs are polymers designed and formulated to exhibit the requisite viscoelastic properties resulting in a desired balance of tack, peel adhesion, and shear holding power. Obtaining the proper balance of properties is not a simple process.

As used herein, medical device refers to an article comprises at least one substrate and an adhesive composition. During use, the adhesive composition is temporality bonded to (e.g. human) skin. The pressure-sensitive adhesive of the present invention are useful in many medical applications such as tapes, bandages, dressings, drapes, athletic tapes, tapes and tabs used in adhering a medical device such as a sensor, electrode, and an ostomy appliance, as well as transdermal drug delivery devices. Additionally, the adhesive may be employed on protective and decorative face masks.

By use of the proper kind and amount of polydiorganosiloxane polyurea copolymer(s), silicate tackifying resins(s), and diluent(s), as described herein, the adhesive characteristicly feels "soft" to the touch and has a gel-like consistency. The softness of the adhesive can be characterized to at least some extent with certain tests. For example the softness can be characterized by Dynamic Mechanical Analysis. Exemplary adhesive compositions of the invention exhibit a storage modulus (G') of no more than about $1\times10^5$ Pa at 25° C. Preferably, the storage modulus (G') is about $1\times10^4$ Pa at 25° C. or less. The adhesive may have a storage modulus (G') of any integer between $1\times10^5$ Pa and $1\times10^4$ Pa. An advantage of the adhesive compositions of the present invention is that the storage modulus exhibits a plateau region from about 25° C. to temperatures of 50° C. and even 100° C. For adhesives for medical devices, the adhesive also exhibits adequate adhesion to (e.g. human) skin. Polypropylene test panels are often employed to simulate adhesion to skin. The adhesive composition preferably exhibits an 180° peel adhesion to polypropylene according to the test method described in the forthcoming examples of at least 3 g/linear inch (2.54 cm). Preferably the 180° peel adhesion to polypropylene is at least 5 to 10 g/linear inch (2.54 cm). Advantageously, the adhesive of the invention is less aggressive. Accordingly, the 180° peel adhesion to polypropylene is less than 1000 g/linear inch (2.54 inch), preferably less than 500 g/linear inch (2.54 inch), and more preferably less than 200 g/linear inch (2.54 cm) (e.g. less than 100 g/linear inch (2.54 cm)). Another advantage is that the adhesive can be reapplied to skin after being removed. Further, the adhesive can be cleanly removed without removing hair because of its softness.

The adhesive can be coated onto any backing suitable for medical uses including porous and nonporous backings. The substrates (i.e., backings) are preferably flexible yet resistant to tearing. The thickness of the substrate is typically at least 0.0125 mm. In general, the thickness of the substrate is no greater than 3 mm. The substrate may have a basis weight of at least 5 grams/meter$^2$. Further, the substrate typically has a basis weight of no greater than 200 grams/meter$^2$.

Suitable substrates include fabric, non-woven or woven polymeric webs, polymer films, hydrocolloids, foam, metallic foils, paper, and/or combinations thereof.

For some embodiments it is desirable to use an open apertured substrate (e.g., a scrim). The apertures (i.e., openings) in the porous substrates are of sufficient size and sufficient number to facilitate mechanical bonding of the adhesive and the backing. As an additional benefit such construction is typically highly breathable. A scrim typically comprises a plurality of warp elements and a plurality of weft elements that are woven or knitted together to form the scrim. The warp elements extend longitudinally along the backing layer and are uniformly transversely spaced from one another. The weft elements extend transversely along the backing layer typically at right angles to the warp elements. Other open structures that are either woven or nonwoven (e.g. meltblow) may also be employed. For other embodiments it is preferred to employ a tie layer between the adhesive and the backing as will subsequently be described.

Materials of the backing or support substrate include a wide variety of materials including paper, natural or synthetic fibers, threads and yarns made from materials such as cotton, rayon, wool, hemp, jute, nylon, polyesters, polyacetates, polyacrylics, alginates, ethylene-propylene-diene rubbers, natural rubber, polyesters, polyisobutylenes, polyolefins (e.g., polypropylene polyethylene, ethylene propylene copolymers, and ethylene butylene copolymers), polyurethanes (including polyurethane foams), vinyls including polyvinylchloride and ethylene-vinyl acetate, polyamides, polystyrenes, fiberglass, ceramic fibers, and/or combinations thereof.

The backing can also be provided with stretch-release properties. Stretch-release refers to the property of an adhesive article characterized in that, when the article is pulled from a surface, the article detaches from the surface without leaving significant visible residue. For example, a film backing can be formed from a highly extensible and highly elastic composition that includes elastomeric and thermoplastic A-B-A block copolymers, having a low rubber modulus, a lengthwise elongation to break of at least 200%, and a 50% rubber modulus of not above 2,000 pounds/square inch (13.8 megapascals (MPa)). Such backings are described in U.S. Pat. No. 4,024,312 (Korpman). Alternatively, the backing can be highly extensible and substantially non-recoverable such as those described in U.S. Pat. No. 5,516,581 (Kreckel et al.).

The adhesive composition preferably comprises an unreactive mixture of at least one polydiorganosiloxane polyurea copolymer, at least one unreactive diluent, and at least one silicate tackifying resin. In such preferred embodiment, the polydiorganosiloxane polyurea copolymer preferably comprises unreactive end groups. An unreactive mixture is preferred due to exhibiting stable adhesive properties even after aging. Stable adhesive properties refers to cleanly removing from (e.g. human) skin and/or a polypropylene substrate as subsequently described without leaving a sticky residue. Alternatively, for articles suitable for temporary use and/or having a shorter shelf life, the polydiorganosiloxane polyurea copolymer may optionally comprise end groups having ethylenic unsaturation.

As used herein, copolymer refers to polymers containing two or more different monomers, including terpolymers, tetrapolymers, etc. Preferred polydiorganosiloxane polyurea copolymers suitable for use in the preparation of adhesives according to the present invention are the reaction products of at least one polyamine, wherein the polyamine includes at least one polydiorganosiloxane polyamine (preferably, diamine) with at least one polyisocyanate, and an optional polyfunctional chain extender such as an organic amine and/or alcohol. The mole ratio of isocyanate to amine is preferably in a range of about 0.9:1 to about 1.1:1, more preferably about 0.95:1 to about 1.05:1, and most preferably about 0.97:1 to about 1.03:1. That is, preferred polydiorganosiloxane polyurea copolymers suitable for use in the preparation of pressure sensitive adhesives according to the present invention have polydiorganosiloxane units, polyisocyanate residue units, and, optionally, organic polyamine and/or polyol residue units. The polyisocyanate residue units and the polyamine residue units preferably form less than 15% by weight, and more preferably, less than 5% by weight, of the of the polydiorganosiloxane polyurea copolymer. The polyisocyanate residue is the polyisocyanate minus the —NCO groups and the polyamine residue is the polyamine minus the —NH$_2$ groups. The polyisocyanate residue is connected to the polyamine residue by urea linkages. The polyisocyanate residue is connected to the polyol residue by urethane linkages. Examples of such segmented copolymers are disclosed in U.S. Pat. No. 5,461,134 (Leir et al.) and International Publication Nos. WO 96/34029, WO 96/35458, and WO 98/17726.

Preferred polydiorganosiloxane polyurea copolymers, used in preparing the adhesive of the present invention, can be represented by the repeating unit (Formula I):

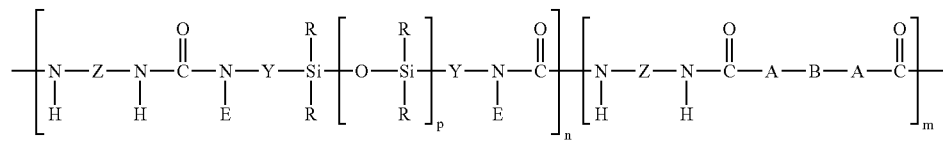

where:

each R is independently an alkyl moiety (preferably having 1 to 12 carbon atoms and may be substituted with, for example, trifluoroalkyl or vinyl groups), a vinyl moiety or higher alkenyl moiety (preferably represented by the formula —R$^2$(CH$_2$)$_a$CH=CH$_2$ wherein R$^2$ is —(CH$_2$)$_b$— or —(CH$_2$)$_c$CH=CH— and a is 1, 2, or 3, b is 0, 3, or 6, and c is 3, 4, or 5), a cycloalkyl moiety (preferably having 6 to 12 carbon atoms and may be substituted with, for example, alkyl, fluoroalkyl, or vinyl groups), or an aryl moiety (preferably having 6 to 20 carbon atoms and may be substituted with, for example, alkyl, cycloalkyl, fluoroalkyl or vinyl groups), or R is a fluorine-containing group (including those described in U.S. Pat. No. 5,236,997 (Fijiki), perfluoroalkyl groups as described in U.S. Pat. No. 5,028,679 (Terae et al.), or perfluoroether-containing groups, as described in U.S. Pat. No.

4,900,474 (Terae et al.) and U.S. Pat. No. 5,118,775 (Inomata et al.)); preferably at least 50% of the R moieties are methyl moieties with the balance being monovalent alkyl or substituted alkyl moieties having 1 to 12 carbon atoms, alkenylene moieties, phenyl moieties, or substituted phenyl moieties;

each Z is independently a polyvalent moiety that is an arylene moiety, an aralkylene moiety, an alkylene moiety, or a cycloalkylene moiety (each of which preferably has 6 to 20 carbon atoms); preferably Z is 2,6-tolylene, 4,4'-methylenediphenylene, 3,3'-dimethoxy-4,4'-biphenylene, tetramethyl-m-xylylene, 4,4'-methylenedicyclohexylene, 3,5,5-trimethyl-3-methylenecyclohexylene, 1,6-hexamethylene, 1,4-cyclohexylene, 2,2,4-trimethylhexylene, and mixtures thereof;

each Y is independently a polyvalent moiety that independently is an alkylene moiety (preferably having 1 to 10 carbon atoms), an aralkylene moiety or an arylene moiety (each of which preferably has 6 to 20 carbon atoms);

each E is independently hydrogen, an alkyl moiety of 1 to 10 carbon atoms, phenyl, or a moiety that completes a ring structure including Y to form a heterocycle;

each A is independently oxygen or —N(G)—, wherein each G is independently hydrogen, an alkyl moiety of 1 to 10 carbon atoms, phenyl, or a moiety that completes a ring structure including B to form a heterocycle;

B is an alkylene, aralkylene, cycloalkylene, phenylene, polyalkylene, polyalkylene oxide (including for example, polyethylene oxide, polypropylene oxide, polytetramethylene oxide, polycaprolactone, polyethylene adipate), copolymers, or mixtures thereof, or a moiety completing a ring structure including A to form a heterocycle;

m is a number that is 0 to about 1000, preferably 0 to about 25;

n is a number that is equal to or greater than 1 (preferably, n is greater than 8); and p is a number that is about 5 or larger, preferably, about 15 to about 2000, more preferably, about 70 to about 1500, and most preferably about 150 to about 1500.

In the use of polyisocyanates when Z is a moiety having a functionality greater than 2 and/or polyamines when B is a moiety having a functionality greater than 2, the structure of Formula I will be modified to reflect branching at the polymer backbone.

Different isocyanates in the reaction will modify the properties of the polydiorganosiloxane polyurea copolymers in varying ways. Diisocyanates useful in the process of the present invention can be represented by the following (Formula II):

OCN-Z-NCO

Any diisocyanate that can react with a polyamine, and in particular with polydiorganosiloxane diamine of Formula III, below, can be used in the present invention. Examples of such diisocyanates include, but are not limited to, aromatic diisocyanates, such as 2,6-toluene diisocyanate, 2,5-toluene diisocyanate, 2,4-toluene diisocyanate, m-phenylene diisocyanate, p-phenylene diisocyanate, methylene bis(o-chlorophenyl diisocyanate), methylenediphenylene-4,4'-diisocyanate, polycarbodiimide-modified methylenediphenylene diisocyanate, (4,4'-diisocyanato-3,3',5,5'-tetraethyl) diphenylmethane, 4,4'-diisocyanato-3,3'-dimethoxybiphenyl(o-dianisidine diisocyanate), 5-chloro-2,4-toluene diisocyanate, 1-chloromethyl-2,4-diisocyanato benzene, aromatic-aliphatic diisocyanates such as m-xylylene diisocyanate, tetramethyl-m-xylylene diisocyanate, aliphatic diisocyanates, such as 1,4-diisocyanatobutane, 1,6-diisocyanatohexane, 1,12-diisocyanatododecane, 2-methyl-1,5-diisocyanatopentane, and cycloaliphatic diisocyanates such as methylenedicyclohexylene-4,4'-diisocyanate, 3-isocyanatomethyl-3,5,5-trimethylcyclohexyl isocyanate (isophorone diisocyanate), 2,2,4-trimethylhexyl diisocyanate, and cyclohexylene-1,4-diisocyanate and mixtures thereof.

Preferred diisocyanates include 2,6-toluene diisocyanate, methylenediphenylene-4,4'-diisocyanate, polycarbodiimide-modified methylenediphenyl diisocyanate, 4,4'-diisocyanato-3,3'-dimethoxybiphenyl(o-dianisidine diisocyanate), tetramethyl-m-xylylene diisocyanate, methylenedicyclohexylene-4,4'-diisocyanate, 3-isocyanatomethyl-3,5,5-trimethylcyclohexyl isocyanate (isophorone diisocyanate), 1,6-diisocyanatohexane, 2,2,4-trimethylhexyl diisocyanate, and cyclohexylene-1,4-diisocyanate.

Polydiorganosiloxane polyamines useful in the process of the present invention are preferably diamines, which can be represented by the following (Formula III):

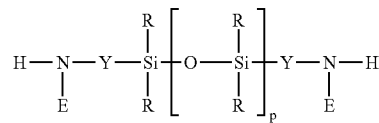

wherein each of R, Y, E, and p are defined as above. Generally, the number average molecular weight of the polydiorganosiloxane polyamines useful in the present invention is greater than about 700.

Preferred polydiorganosiloxane diamines (also referred to as silicone diamines) useful in the present invention are any which fall within Formula III above and including those having number average molecular weights in the range of about 5000 to about 150,000. Polydiorganosiloxane diamines are disclosed, for example, in U.S. Pat. No. 3,890,269 (Martin), U.S. Pat. No. 4,661,577 (JoLane et al.), U.S. Pat. No. 5,026,890 (Webb et al.), U.S. Pat. No. 5,214,119 (Leir et al.), U.S. Pat. No. 5,276,122 (Aoki et al.), U.S. Pat. No. 5,461,134 (Leir et al.), and U.S. Pat. No. 5,512,650 (Leir et al.).

Polydiorganosiloxane polyamines are commercially available from, for example, Shin-Etsu Silicones of America, Inc., Akron, Ohio, and Hüls America, Inc., Pitscataway, N.J. Preferred are substantially pure polydiorganosiloxane diamines prepared as disclosed in U.S. Pat. No. 5,214,119 (Leir et al.). The polydiorganosiloxane diamines having such high purity are prepared from the reaction of cyclic organosilanes and bis(aminoalkyl)disiloxanes utilizing an anhydrous amino alkyl functional silanolate catalyst such as tetramethylammonium-3-aminopropyldimethyl silanolate, preferably in an amount less than 0.15 weight percent based on the weight of the total amount of cyclic organosiloxane with the reaction run in two stages. Particularly preferred polydiorganosiloxane diamines are prepared using cesium and rubidium catalysts and are disclosed in U.S. Pat. No. 5,512,650 (Leir et al.).

Examples of polydiorganosiloxane polyamines useful in the present invention include, but are not limited to, polydimethylsiloxane diamine, polydiphenylsiloxane diamine, polytrifluoropropylmethylsiloxane diamine, polyphenylmethylsiloxane diamine, polydiethylsiloxane diamine, polydivinylsiloxane diamine, polyvinylmethylsiloxane diamine, poly(5-hexenyl)methylsiloxane diamine, and copolymers and mixtures thereof.

The polydiorganosiloxane polyamine component employed to prepare polydiorganosiloxane polyurea segmented copolymers of this invention provides a means of adjusting the modulus of elasticity of the resultant copolymer. In general, high molecular weight polydiorganosiloxane polyamines provide copolymers of lower modulus, whereas low molecular weight polydiorganosiloxane polyamines provide polydiorganosiloxane polyurea segmented copolymers of higher modulus.

When polydiorganosiloxane polyurea segmented copolymer compositions contain an optional organic polyamine, this optional component provides yet another means of modifying the modulus of elasticity of copolymers of this invention. The concentration of organic polyamine as well as the type and molecular weight of the organic polyamine determine how it influences the modulus of polydiorganosiloxane polyurea segmented copolymers containing this component.

Examples of organic polyamines useful in the present invention include but are not limited to polyoxyalkylene diamine, such as D-230, D-400, D-2000, D-4000, DU-700, ED-2001 and EDR-148, all available from Huntsman Chemical Corp., Salt Lake City, Utah, polyoxyalkylene triamine, such as T-3000 and T-5000 available from Huntsman, polyalkylene diamines such as DYTEK A and DYTEK EP, available from DuPont, Wilmington, Del., 1,4-bis(3-aminopropyl) piperazine, (3,3'-diamino-N-methyl-dipropylamine) both available from Aldrich Chemical Co., Milwaukee, Wis., and mixtures thereof.

The nature of the isocyanate residue in the polydiorganosiloxane polyurea copolymer influences stiffness and flow properties, and also affects the properties of the mixtures. Isocyanate residues resulting from diisocyanates that form crystallizable ureas, such as tetramethyl-m-xylylene diisocyanate, 1,12-dodecane diisocyanate, and dianisidine diisocyanate, provide mixtures that can be stiffer, if sufficient polydiorganosiloxane polyurea copolymer is used, than those prepared from methylenedicyclohexylene-4,4'-diisocyanate, 3-isocyanatomethyl-3,5,5-trimethylcyclohexyl isocyanate, and m-xylylene diisocyanate.

Crosslinking agents, if desired may be used, for example Si—H-containing agents may be used to crosslink curable polydiorganosiloxane polyurea copolymers or photoinitiators can be used for free-radically curable polydiorganosiloxane urea copolymers. Additional curatives may also be present such as hydrosilation curatives, peroxide curatives, and photocuratives, such as triazines. When used, the amounts of such components are those that are suitable for the purpose intended and are typically used at a concentration of from about 0.1% to about 5% by weight of the total weight of the polymerizable composition. Crosslinking can also be carried out using electron beam radiation if desired.

Alternatively, but less preferred, the polydiorganosiloxane polyurea copolymer may comprise reactive end groups. For example, the polydiorganosiloxane polyurea copolymer may have the same general formula as Formula III as previously described with the exception that the hydrogen end groups are replaced with a ultraviolet (UV) curable end group represented by the following (Formula IV):

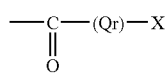

X is a group having ethylenic unsaturations;
Q is a divalent linking group; and
r is an integer of 0 to 1.

Regardless of whether the end groups of polydiorganosiloxane polyurea copolymer(s) are UV curable or unreactive, the polydiorganosiloxane polyurea copolymer is generally prepared such that the molar ratio of diamine to diisocyanate is maintained in the range of about 1.0:0.95 to 1.0:1.05. By use of a relatively high molecular weight diamine in combination with a molar ratio of about 1 to 1, the resulting polydiorganosiloxane polyurea copolymer has a high molecular weight.

The adhesive of the invention may comprise a mixture of more than one of the polydiorganosiloxane polyurea copolymers just described. For example, the adhesive may comprises a blend of two polydiorganosiloxane polyurea copolymers, each having unreactive end groups, wherein the first copolymer has a higher molecular weight than the second copolymer. As another example, the adhesive may comprises a blend of two polydiorganosiloxane polyurea copolymers, wherein the first copolymer comprises end group(s) having ethylenic unsaturation and the second copolymer comprise unreactive end groups.

The polydiorganosiloxane polyurea copolymers can be made by any of a variety of known methods, including solvent-based and solvent-free methods. Examples of solvent-based processes include Tyagi et al., "Segmented Organosiloxane Copolymers: 2. Thermal and Mechanical Properties of Siloxane urea Copolymers," *Polymer*, Vol. 25, December, 1984 and U.S. Pat. No. 5,214,119 (Leir et al.). Suitable solvents are organic solvents that are unreactive with the polyisocyanates and that maintain the reactants and products completely in solution throughout the polymerization reaction. Typical organic solvents include those that have a combination of polar and nonpolar character, or mixtures of polar solvents with nonpolar solvents can be used. Preferred organic solvents include polar aprotic solvents, chlorinated solvents, ethers, aromatic hydrocarbons, aliphatic hydrocarbons, and alcohols. Examples include heptane, toluene, xylene, methyl ethyl ketone, 2-propanol, tert-butanol, tetrahydrofuran, isoamyl alcohol, chloroform, dichloromethane, dimethyl formamide, and the like, and combinations thereof. Examples of solvent-free processes are described in International Publication Nos. WO 96/34029, WO 96/35458, and WO 98/17726.

The adhesive composition of the invention comprises greater than 30 wt-% of at least one silicate tackifying resin in order to provide the proper level of adhesion to skin. Typically the amount of silicate tackifying resin is no greater than about 60 wt-%. Preferably, the amount of silicate tackifying resin is at least 40 wt-%. Silicate tackifying resin amounts of any integer between the minimums and maximums can usefully employed.

The silicate tackifying resins useful in the present invention include those resins composed of the following structural units M (R'$_3$SiO$_{1/2}$ units), D (R'$_2$SiO$_{2/2}$ units), T (R'SiO$_{3/2}$ units), and Q(SiO$_{4/2}$ units), and combinations thereof. Typical examples include MQ silicone tackifying resins, MQD silicone tackifying resins, and MQT silicone tackifying resins. These preferably have a number average molecular weight of about 100 to about 50,000, more preferably about 500 to about 15,000 and generally have methyl substituents.

MQ silicone tackifying resins are copolymeric silicone resins having R'$_3$SiO$_{1/2}$ units ("M" units) and SiO$_{4/2}$ units ("Q" units). Such resins are described in, for example, *Encyclopedia of Polymer Science and Engineering*, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248, 739 (Schmidt et al.).

Certain MQ silicone tackifying resins can be prepared by the silica hydrosol capping process described in U.S. Pat. No. 2,676,182 (Daudt et al.) as modified according to U.S. Pat.

No. 3,627,851 (Brady), and U.S. Pat. No. 3,772,247 (Flannigan). The modified process of Daudt et al. includes limiting the concentration of the sodium silicate solution, and/or the silicon-to-sodium ratio in the sodium silicate, and/or the time before capping the neutralized sodium silicate solution to generally lower values than those disclosed by Daudt et al. The neutralized silica hydrosol is preferably stabilized with an alcohol, such as 2-propanol, and capped with $R_3SiO_{1/2}$ siloxane units as soon as possible after being neutralized. It is important to note that the level of silicon bonded hydroxyl groups on the MQ resin may be reduced, preferably to less than about 1.5% by weight, more preferably to no greater than about 1.2 wt-%, even more preferably to no greater than about 1.0 wt-%, and most preferably to no greater than 0.8 wt-%. This may be accomplished, for example, by reacting hexamethyldisilazane with the silicone tackifying resin. Such a reaction may be catalyzed, for example, with trifluoroacetic acid. Alternatively, trimethylchlorosilane or trimethylsilylacetamide may be reacted with the silicone tackifying resin, a catalyst not being necessary in this case.

Suitable silicate tackifying resins are commercially available from sources such as Dow Corning, Midland, Mich., General Electric Silicones Waterford, N.Y. and Rhodia Silicones, Rock Hill, S.C. Examples of particularly useful MQ silicone tackifying resins include those available under the trade designations SR-545 and SR-1000, both of which are commercially available from GE Silicones, Waterford, N.Y. Such resins are generally supplied in organic solvent and may be employed in the adhesives of the present invention as received.

The adhesive composition comprises greater than 10 wt-% of at least one unreactive diluent. By unreactive it is meant that the diluent does not react with the silicate tackifying resin or the polydiorganosiloxane polyurea copolymer(s) of the adhesive composition. The diluent does not react with such component during manufacture of the adhesive, during application of the adhesive to a substrate, or upon aging. Typically, the diluent is substantially free of reactive groups. Typically the amount of diluent is no greater than 50 wt-%. Preferably, the amount of diluent is at least 20 wt-% and more preferably at least 30 wt-%. Diluent amounts of any integer between the minimums and maximums can be employed.

Useful unreactive diluents are compatible with the polydiorganosiloxane polyurea copolymers, such that the diluent does not phase separate. A means of detecting phase separation (i.e. afterwards) is by the presence of a sticky residue left on the skin after removal of the medical device from skin or the presence of a sticky residue upon removal of adhesive coated substrate from polypropylene test substrate (i.e. as further described in the forthcoming examples.)

Preferred diluents typically have a number average molecular weight of at least about 150 g/mole and more preferably at least about 500 g/mole. The molecular weight of the diluent is preferably less than 100,000 g/mole, more preferably less than about 50,000 g/mole, and in some embodiment preferably less than about 30,000 g/mole. For amounts of diluent of about 40 wt-% or greater the molecular weight is preferably less than about 20,000 g/mole. The molecular weight of the diluent may be measured or reported by the supplier (e.g. GE Silicones, Waterford, N.Y.). In some embodiments the molecular weight of the unreactive diluent is less than the molecular weight of the diamine employed to make the polydiorganosiloxane polyurea copolymer.

A preferred unreactive diluent is a silicone oil. Representative silicone oils include but are not limited to trialkylsiloxy terminated polydimethylsiloxane, polyphenylmethylsoloxane, polydialkylsiloxane, as well as copolymers of such with trialkylsiloxy terminated species.

Other suitable diluents include for example hydrocarbon fluids, low molecular weight oligomers and oils. Selection of such other suitable diluents shall be based on compatibility. Further, for medical devices, care will also be taken to selected diluents that are not known to be skin irritants such as mineral oil for example. Various combinations of diluents can be used if desired.

The pressure sensitive adhesives of the present invention can include one or more additives. For example, dyes or pigments may be added as colorant; electrically and/or thermally conductive compounds may be added to make an adhesive electrically and/or thermally conductive or antistatic; antioxidants and bacteriostatic agents may be added; and UV light stabilizers and absorbers, such as hindered amine light stabilizers (HALS), may be added to stabilize the PSA against UV degradation and to block certain UV wavelengths from passing through the article. Other additives include adhesion promoters, fillers, tack enhancers, glass or ceramic microbubbles, expanded and unexpanded polymeric microspheres, blowing agents, polymers, and other property modifiers, such as clays, flame retardants, and compatibilizers. These additives can be used in various combinations in amounts of about 0.05 weight percent to about 3 weight percent, based on the total weight of the adhesive composition.

The adhesive composition can be applied to appropriate release liners or directly to a substrate (e.g. tape backings) by a wide range of processes, including, solution coating, solution spraying, hot melt coating, extrusion, coextrusion, lamination, pattern coating, etc., to make adhesive laminates.

Commercially available liners include liners having a fluorosilicone release coating such as commercially available from Dow Corning Corp., Midland, Mich. under the trade designation "Dow Corning SYL-OFF Q2-7785"; commercially available from Shin-Etsu Silicones of America, Inc., Torrance, Calif. under the trade designation "X-70-029NS"; and commercially available from Release International, Bedford Park, Ill. under the trade designation "S TAKE-OFF 2402", and the like.

The articles of the invention may contain additional layers such as primers, barrier coatings, tie layers, and combinations thereof. Priming of the layer(s) may include a priming step such as chemical or mechanical priming. In the case of non-porous backing wherein the mechanical bonding with the backing is lacking or insufficient, it is preferred to include a tie layer between the pressure sensitive adhesive composition in the backing.

The tie layer preferably comprises the same base polymer and resin (i.e. common) as the adhesive composition and further comprises a reinforcement material. A preferred reinforcement material is polymeric fiber. Suitable polymeric fibers include polyolefin (e.g. polyethylene copolymers, terpolymers, and tetrapolymers; polypropylene copolymers), polyamide, polyester, copolyesters, and the like.

The reinforcement material is not appreciably affected by the adhesive composition. In particular, the reinforcement material is not plasticized by the diluent of the adhesive composition and accordingly do not exhibit a substantial decrease in mechanical properties. The tie layer composition is typically substantially free of diluent. Alternatively, the tie layer may comprise a diluent, yet at a concentration significantly less than that of the adhesive. Although tie layers comprised of polydiorganosiloxane polyurea copolymer(s), silicate tackifying resins(s), and polyolefin fibers, are presently disclosed in combination with adhesive compositions comprising the same polymer and resin, it is surmised that the use of tie layers comprising a common base polymer and resin in combination with at least one reinforcement material may be employed with other types of pressure sensitive adhesive compositions (e.g. thermoplastic block copolymer based) as well.

Objects and advantages of this invention are further illustrated by the following examples, but the particular materials and amounts thereof recited in these examples, as well as other conditions and details, should not be construed to unduly limit this invention. All amounts listed in the tape preparations and examples are by weight unless otherwise specified.

The ingredients employed in the Examples are set forth in Table I as follows:

TABLE I

| Abbreviation/Trade Designation | Description |
|---|---|
| SR-545 | A 60% solids solution of MQ resin in toluene commercially available from GE Silicones, Waterford, NY under the trade designation SR-545 |
| DC 2-7066 | A 60% solids solution of MQ resin in toluene commercially available from Dow Corning, Midland, MI under the trade designation DC 2-7066 |
| DMS-T11 | Silicone fluid available from Gelest Inc, Tullytown, PA |
| DMS-T15 | Silicone fluid available from Gelest Inc, Tullytown, PA |
| DMS-T21 | Silicone fluid available from Gelest Inc, Tullytown, PA |
| DMS-T25 | Silicone fluid available from Gelest Inc, Tullytown, PA |
| DMS-T31 | Silicone fluid available from Gelest Inc, Tullytown, PA |
| DMS-T35 | Silicone fluid available from Gelest Inc, Tullytown, PA |
| DMS-T46 | Silicone fluid available from Gelest Inc, Tullytown, PA |
| DMS-T51 | Silicone fluid available from Gelest Inc, Tullytown, PA |
| H-MDI | Methylenedicyclohexylene-4,4'-diisocyanate, available under the trade designation DESMODUR W H12MDI from Bayer: Pittsburgh, PA |
| IPDI | Isophorone diisocyanate commercially available from Olin Chemicals Co, Stamford, CN |
| POE 10 | Ultra Low Density Linear Poly(ethylene-co-octene) ATTANE 4202 commercially available from Dow Chemical Co.; Midland, MI. |
| DYTEK A | An organic diamine, commercially available from DuPont: Wilmington, DE |
| IEM | 2-isocyanatoethylmethacrylate available from Aldrich Chemical Co., Milwaukee, WI |
| PDMS diamine | Made by procedure described in Example 2 of U.S. Pat. No. 5,512,650. |
| SPU elastomers | Silicone polyurea elastomer made as indicated in examples. |

Test Methods

180° Peel Adhesion

This peel adhesion test is similar to the test method described in ASTM D 3330-90, substituting a polypropylene (PP) substrate or high-density polyethylene (HDPE), both of which are commercially available from Aeromat Plastics, Burnsville, Minn., in place of the stainless steel substrate described in the test.

Adhesive coatings on an aminated-polybutadiene primed polyester film of polyethylene terephthalate having a thickness of 38 micrometers PET film were cut into 1.27 centimeter by 15 centimeter strips. Each strip was then adhered to a 10 centimeter by 20 centimeter clean, solvent washed polypropylene panel using a 2-kilogram roller passed once over the strip. The bonded assembly dwelled at room temperature for about one minute and was tested for 180° peel adhesion using an IMASS slip/peel tester (Model 3M90, commercially available from Instrumentors Inc., Strongsville, Ohio) at a rate of 2.3 meters/minute (90 inches/minute) or 30.5 centimeters/minute (12 inches/minute) over a five second data collection time. Two samples were tested; the reported peel adhesion value is an average of the peel adhesion value from each of the two samples and the failure mode was recorded—adhesive at PP, cohesive or adhesive at PET.

Dynamic Mechanical Analysis (DMA)

The storage (G') and loss (G") shear moduli were determined using a Rheometrics ARES rheometer operated in the strain controlled oscillatory mode. The ARES rheometer (available from TA Instruments, New Castle, Del.) was equipped with 8 mm parallel plates surrounded with a forced air convection oven for temperature control.

Preparation of Adhesive Compositions

I. Preparation of Silicone Polyurea Solution (SPU Elastomer)

In a reaction vessel was placed 330 parts of PDMS diamine 33,000 that was degassed at 100° C. under reduced pressure to remove absorbed carbon dioxide, and an equal molar ratio of DYTEK A (1.86 parts). A mixture of toluene/2-propanol (70/30 by weight) was added to make diamine mixture solution (1693 g). Then the solution was stirred at room temperature, 6.71 parts of H-MDI was added and the resulting mixture was stirred for two hours to give a high molecular weight SPU elastomer solution (20% solid).

Silcone fluids of various molecular weights were used to make adhesive compositions of the examples. The molecular weights of these fluids is provided in Table II as follows:

EXAMPLE 1

70 parts silicone fluid DMS-T11 and 150 parts of SPU elastomer solution (30 parts of solid) were mixed with 166.7 parts of silicone tackifier SR-545 (100 parts of solid) to prepare a pressure sensitive adhesive (PSA). This PSA was diluted with 280 parts of toluene/isopropanol mixture (70/30 wt) to prepare a PSA solution (30% solid). The PSA solution was then coated on the PET film using a knife coater and the wet gap was controlled to be 8 mil. The coated PSA was dried at 70° C. for 20 minutes to get PSA dry film of about 2 mil.

EXAMPLES 2-7

Examples 2-7 were prepared as in Example 1 except that a different molecular weight silicone fluid was used as indicated in following Table II.

EXAMPLE 8

80 parts silicone fluid DMS-T11 and 100 parts of SPU elastomer solution (20 parts of solid) were mixed with 166.7 parts of silicone tackifier SR-545 (100 parts of solid) to prepare a pressure sensitive adhesive (PSA). This PSA was diluted and coated as described in Example 1.

EXAMPLES 9-13

Examples 9-13 were prepared as in Example 8 except that a different molecular weight silicone fluid was used as indicated in following Table II.

TABLE II

| Example No. | Silicone Fluid | Mw of Silicone Fluid | Silicone Fluid wt-% | SPU Elastomer wt-% | SR-545 solid) wt-% |
|---|---|---|---|---|---|
| 1 | DMS-T11 | 1,250 | 35 | 15 | 50 |
| 2 | DMS-T15 | 3,780 | 35 | 15 | 50 |
| 3 | DMS-T21 | 5,970 | 35 | 15 | 50 |
| 4 | DMS-T25 | 17,250 | 35 | 15 | 50 |
| 5 | DMS-T31 | 28,000 | 35 | 15 | 50 |

TABLE II-continued

| Example No. | Silicone Fluid | Mw of Silicone Fluid | Silicone Fluid wt-% | SPU Elastomer wt-% | SR-545 solid) wt-% |
|---|---|---|---|---|---|
| 6 | DMS-T35 | 49,350 | 35 | 15 | 50 |
| 7 | DMS-T46 | 116,500 | 35 | 15 | 50 |
| 8 | DMS-T11 | 1,250 | 40 | 10 | 50 |
| 9 | DMS-T15 | 3,780 | 40 | 10 | 50 |
| 10 | DMS-T21 | 5,970 | 40 | 10 | 50 |
| 11 | DMS-T25 | 17,250 | 40 | 10 | 50 |
| 12 | DMS-T31 | 28,000 | 40 | 10 | 50 |
| 13 | DMS-T35 | 49,350 | 40 | 10 | 50 |

The samples were conditioned at 25° C./50% relative humidity for 24 hours before peel test. Examples 1-13 were tested for adhesive performance. The results of peel force and failure mode obtained are reported in Table III.

TABLE III

| Example | Peel Force from PP Panel (g/in) | Failure Mode From PP Panel | Failure Mode from Skin |
|---|---|---|---|
| 1 | 13.6 | Adhesive | Clean |
| 2 | 23.2 | Adhesive | Clean |
| 3 | 24.2 | Adhesive | Clean |
| 4 | 32.2 | Adhesive | Clean |
| 5 | 35.6 | Adhesive | Clean |
| 6 | 124 | Cohesive | Low adhesion to skin |
| 7 | 28.8 | Cohesive | Very low adhesion to skin |
| 8 | 15.4 | Adhesive | Clean |
| 9 | 20.8 | Adhesive | Clean |
| 10 | 26.2 | Adhesive | Clean |
| 11 | 48.4 | Adhesive | Clean |
| 12 | 79.5 | Adhesive | Sticky residue left |
| 13 | 40.2 | Cohesive | More sticky residue |

Preparation of Tie Layer

A silicone diamine was made by the procedure generally described in Example 2 of U.S. Pat. No. 5,512,650 with a molecular weight of approximately 77,000 g/mole. This silicone diamine (14.96 parts) was charged to a glass reactor and mixed with 39.00 parts of toluene and 21.00 parts of 2-propanol. The resulting solution was then mixed with 25.00 parts of SR-545. The solution was stirred at room temperature and 0.04 parts of IPDI was added. After 6 hours the solution had become viscous. The resulting solution had a silicone polyurea to MQ resin weight ratio of 50:50. This solution was cast on liners and dried at room temperature to produce a solid tie layer intermediate sample.

A sample of the solid tie layer intermediate sample (225 g) was hot-melt mixed with 25 g of POE 10 resin in a single screw extruder equipped with a 250-milliliter bowl mixer (available from C.W. Brabender Instruments, Inc., South Hackensack, N.J.) at 150° C. for 10 minutes to produce a homogeneous mixture. The tie layer composition was hot-melt coated using a ¾ inch (1.9 cm) single screw extruder available from Haake of Karlsruhe, Germany under the trade designation "Haake Rheocord" onto a fluorinated silicone release liner commercially available from Loparex Inc., Bedford Park, Ill. under the trade designation "REXAM No. 20987" at a thickness of 3 mils. The tie layer composition was transfer coated onto a rayon nonwoven backing, such backing is present on medical tape commercially available from 3M Company under the trade designation "Micropore".

EXAMPLE 14

A PSA film was made as in Example 1 only it was coated on the REXAM No. 20987" rather than PET. The coated PSA was dried at 70° C. for 20 minutes to get PSA dry film of about 2 mil. The dried adhesive film was then laminated at room temperature to the tie layer/nonwoven backing construction to produce a medical tape.

Example 15 was prepared as in Example 14 only the PSA film used was as made in Example 2.

Example 16 was prepared as in Example 14 only the PSA film used was as made in Example 3.

Example 17 was prepared as in Example 14 only the PSA film used was as made in Example 4.

Example 18 was prepared as in Example 14 only the PSA film used was as made in Example 5.

Example 19 was prepared as in Example 14 only the PSA film used was as made in Example 6.

Example 20 was prepared as in Example 14 only the PSA film used was as made in Example 7.

The laminated samples were conditioned at 25° C./50% relative humidity for 24 hours before peel test. The peel force was measured and recorded along with the failure mode as reported in following Table IV.

TABLE IV

| Exp | Peel Force from PP Panel (g/in) | Failure Mode From PP Panel | Failure Mode from Skin |
|---|---|---|---|
| 14 | 18.1 | Adhesive | Clean |
| 15 | 26.2 | Adhesive | Clean |
| 16 | 29.3 | Adhesive | Clean |
| 17 | 32.6 | Adhesive | Clean |
| 18 | 35.8 | Adhesive | Clean |
| 19 | 128.0 | Cohesive | Low adhesion to skin |
| 20 | 29.0 | Cohesive | Very low adhesion to skin |

EXAMPLE 21

In a reaction vessel was placed 7.50 parts of PDMS diamine 14,000 and 7.50 parts of PDMS diamine 33,000. After mixing, 0.23 parts of IEM was added. To this mixture was added 1.00 part of a photoiniatiator commercially available from Speciality Chemical Corp, Tarrytown, N.Y. under the trade designation "Darocur 1173". This was mixed for 2 hours and next was added 35.0 parts polydimethylsiloxane commercially available from Rodia Inc., Rock Hill, S.C. under the trade designation "Rhodorsil Fluid 47V-500". After mixing, 50 parts of the DC 2-7066 solution was added. This was mixed for 1 hour and then cast onto PET and dried in an oven at 70° C. for 10 minutes to yield a 2 mil thick film when dry. The Rexham release liner was next laminated to the dried PSA and the laminated structure was placed under UV lights for 30 minutes to cure the elastomer mixture. After the cure was complete, the liner was removed and the sample was tested. The test results were as follows:

The cured adhesive composition was clear having slight finger tack (i.e. 1 on a scale of 1-3 scale. The peel from polypropylene was 8 g/linear inch (2.54 cm).

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows

What is claimed is:

1. A medical device comprising:
   a substrate; and
   a pressure sensitive adhesive composition disposed on the substrate;
   wherein the adhesive exhibits a 180° peel adhesion force from polypropylene of less than 100 g/linear inch at a rate of 90 inches per minute and the adhesive composition comprises an unreactive mixture of
      about 10 wt-% to about 20 wt-% polydiorganosiloxane polyurea copolymer;
      30 wt-% to 50 wt-% of a diluent, wherein the diluent has a number average molecular weight of no more than about 30,000 g/mole; and
      greater than 30 wt-% to less than about 60 wt-% of silicate tackifying resin.

2. The medical device of claim 1 wherein the diluent is substantially free of functional groups that react with the polydiorganosiloxane polyurea copolymer and silicate tackifying resin of the adhesive composition.

3. The medical device of claim 1 wherein the polydiorganosiloxane polyurea copolymer comprises unreactive end groups.

4. The medical device of claim 1 wherein the polydiorganosiloxane polyurea copolymer comprises end groups having ethylenic unsaturation.

5. The medical device of claim 1 wherein the diluent is a silicone fluid.

6. The medical device of claim 1 further comprising a tie layer disposed between the substrate and the adhesive.

7. The medical device of claim 6 wherein the tie layer composition comprises the same components as the adhesive and further comprises polymeric fibers.

8. The medical device of claim 1 wherein the adhesive has a loss modulus of no greater than $1 \times 10_5$ Pa at about 25° C.

9. The medical device of claim 1 wherein the adhesive exhibits a peel force from polypropylene of at least 3 g/linear inch (2.54 cm).

10. The medical device of claim 1 wherein the adhesive exhibits a peel force from polypropylene of at least about 10 g/linear inch.

11. The medical device of claim 1 wherein the medical device further comprises a scrim.

12. The medical device of claim 1 wherein the device further comprises a release liner temporarily covering the adhesive.

13. A medical device comprising:
    a substrate; and
    a pressure sensitive adhesive composition disposed on the substrate;
    wherein the adhesive composition comprises an unreactive mixture of
       about 10 wt-% to about 20 wt-% of polydiorganosiloxane polyurea copolymer;
       30 to 50 wt-% of a diluent, wherein the diluent has a number average molecular weight of no more than about 30,000 g/mole; and
       greater than 30 wt-% to less than about 60 wt-% of silicate tackifying resin.

14. The medical device of claim 13 wherein the diluent is a silicone fluid.

15. The medical device of claim 13 wherein the adhesive exhibits a 1800 peel adhesion force from polypropylene of less than 500 g/linear inch at a rate of 90 inches per minute.

16. The medical device of claim 13 wherein the adhesive exhibits a 180° peel adhesion force from polypropylene of less than 200 g/linear inch at a rate of 90 inches per minute.

17. A pressure sensitive adhesive composition comprising an unreactive mixture of
    about 10 wt-% to about 20 wt-% of a polydiorganosiloxane polyurea copolymer;
    30 wt-% to 50 wt-% of a diluent, wherein the diluent has a number average molecular weight of no more than about 30,000 g/mole; and
    greater than 30 wt-% to less than 60 wt-% of silicate tackifying resin.

* * * * *

UNITED STATES PATENT AND TRADEMARK OFFICE
CERTIFICATE OF CORRECTION

PATENT NO. : 7,407,709 B2  Page 1 of 1
APPLICATION NO. : 10/744212
DATED : August 5, 2008
INVENTOR(S) : Zhiming Zhou It is certified that error appears in the above-identified patent and that said Letters Patent is hereby corrected as shown below:

Column 1
Line 57, Delete "ale" and insert -- are --, therefor.

Column 15
Line 5, After "follows" insert -- . --.
Line 42, In Claim 8, delete "1 x $10_5$" and insert -- 1 x $10^5$ --, therefor.

Column 16
Line 28, In Claim 15, delete "1800" and insert -- 180° --, therefor.

Signed and Sealed this

Seventh Day of October, 2008

JON W. DUDAS
*Director of the United States Patent and Trademark Office*